United States Patent
Kong et al.

(10) Patent No.: US 8,521,451 B2
(45) Date of Patent: Aug. 27, 2013

(54) METHOD AND APPARATUS FOR MEASURING OIL VISCOSITY

(75) Inventors: Ho Sung Kong, Seoul (KR); Hung Gu Han, Seoul (KR); Liubou Vasilievna Markova, Gomel (BY); Mikhail Savich Semenyuk, Gomel (BY); Vladimir Mikhailovich Makarenko, Gomel (BY)

(73) Assignee: Korea Institute of Science and Technology, Seoul (KR)

( * ) Notice: Subject to any disclaimer, the term of this patent is extended or adjusted under 35 U.S.C. 154(b) by 223 days.

(21) Appl. No.: 12/978,249

(22) Filed: Dec. 23, 2010

(65) Prior Publication Data

US 2011/0166802 A1 Jul. 7, 2011

(30) Foreign Application Priority Data

Jan. 5, 2010 (KR) ........................ 10-2010-0000473

(51) Int. Cl.
G01F 17/00 (2006.01)
(52) U.S. Cl.
USPC ................ 702/50; 702/25; 702/28; 702/130; 702/54
(58) Field of Classification Search
USPC ................................ 702/50, 25, 28, 54, 130
See application file for complete search history.

(56) References Cited

U.S. PATENT DOCUMENTS

| | | | |
|---|---|---|---|
| 4,741,200 A | 5/1988 | Hammerle | |
| 4,811,593 A | 3/1989 | Miura et al. | |
| 5,741,961 A | 4/1998 | Martin et al. | |
| 6,304,021 B1 | 10/2001 | Wolf et al. | |
| 6,439,034 B1 | 8/2002 | Farone et al. | |
| 7,043,969 B2 | 5/2006 | Matsiev et al. | |
| 7,287,431 B2 | 10/2007 | Liu et al. | |
| 7,391,035 B2 | 6/2008 | Kong et al. | |
| 7,521,945 B2* | 4/2009 | Hedges et al. | 324/698 |
| 2003/0067749 A1* | 4/2003 | Tamba et al. | 361/699 |
| 2005/0209796 A1* | 9/2005 | Kolosov et al. | 702/52 |

FOREIGN PATENT DOCUMENTS

| | | |
|---|---|---|
| JP | 2004-519695 A | 7/2004 |
| KR | 10-1997-0048389 A | 7/1997 |
| KR | 20-1998-0052022 U | 10/1998 |
| WO | WO 95/09353 A1 | 4/1995 |

OTHER PUBLICATIONS

Jain et al., *Magneto-Acoustic Sensors for Measurement of Liquid Temperature, Viscosity, and Density*, Applied Acoustics 62, pp. 1001-1011 (2001).

(Continued)

Primary Examiner — Marc Armand
Assistant Examiner — Ivan Rabovianski
(74) Attorney, Agent, or Firm — NSIP Law

(57) ABSTRACT

Embodiments of a probe for measuring an oil viscosity are provided. In one embodiment, the probe includes a housing, a magnetoelastic ribbon, an electromagnetic coil, a temperature sensor and an electrical board. The housing is mounted to an oil containing member. The magnetoelastic ribbon is fixed to an inside of the housing through a first insert member at one end and is at least partially immersed in the oil at an opposite end. The electromagnetic coil is disposed in the housing to surround the magnetoelastic ribbon. The temperature sensor is mounted to the housing for measuring a temperature of the oil. The electrical board is electrically connected to the electromagnetic coil and the temperature sensor.

8 Claims, 14 Drawing Sheets

(56) References Cited

OTHER PUBLICATIONS

Jain et al., *Effect of Surface Roughness on Liquid Property Measurements using Mechanically Oscillating Sensors,* Sensors and Actuators A 100, pp. 63-69 (2002).

Loiselle et al., *Viscosity Measurements of Viscous Liquids using Magnetoelastic Thick-Film Sensors,* Review of Scientific Instruments, vol. 71 No. 3 (Mar. 2000).

\* cited by examiner

METHOD AND APPARATUS FOR MEASURING OIL VISCOSITY

CROSS-REFERENCE TO RELATED APPLICATIONS

This application claims priority from Korean Patent Application No. 10-2010-0000473 filed on Jan. 5, 2010, the entire disclosure of which is incorporated herein by reference.

TECHNICAL FIELD

The present disclosure relates to a probe for measuring oil viscosity, an apparatus for monitoring oil viscosity including the same and a method of monitoring oil viscosity using the same.

BACKGROUND

An oil viscosity is very important among physicochemical properties of oil. Further, monitoring an oil viscosity allows for detecting change in oil status. If the oil is timely replaced with the change in oil status, then the service lives of mechanical systems can be prolonged and their downtime can be also shortened. Moreover, a maintenance cost of the mechanical systems can decrease and a replacement period for replacing the oil can be extended.

Change in the oil viscosity may precede before critical problems occur in the mechanical systems. Thus, if the change in the oil viscosity could be detected beforehand, then detailed causes of the change in the oil viscosity would be investigated through a laboratorial analysis. Generally, the oil viscosity may increase due to oxidation of the oil, penetration of mixture, generation of air bubbles, etc. Further, oil deterioration may advance along with those factors.

It is well known to those of ordinary skill in the art that the oil viscosity is measured by the laboratory analysis. However, it is difficult to develop a reliable and economical viscosity sensor for measuring the oil viscosity in an on-line or in-line manner.

Monitoring the oil viscosity in real time allows for detecting the following before the mechanical system fails: whether improper oil is used in the mechanical system; whether moisture is mixed into the oil; and whether oil is contaminated with oil-deteriorating products. Further, obtaining data on the oil viscosity in real time eliminates the inconvenience of periodically sampling the oil and measuring the oil viscosity by the laboratory analysis. In particular, human errors associated with sampling the oil can be prevented. Thus, demands for measuring the oil status in real time have recently increased.

An in-line viscometer measures the viscosity of the oil that is used in a tribo system. Thus, the in-line viscometer must have a long service life to work continuously in an aggressive environment (e.g., under conditions of high temperature, high pressure and intensive vibration). Further, the in-line viscometer must provide information on a replacement period and a service life of the oil by reliably measuring a current status of the oil state and then judging the measured values. Furthermore, the in-line viscometer must be compact, economical and precise.

Historically, the in-line viscometer such as a capillary tube viscometer, a rotary viscometer and a falling piston viscometer was developed. However, such in-line viscometers have a complicated structure since they use the measure principle employed in a laboratorial viscometer as it is. Accordingly, new methods and studies for solving such a problem have been devised and made in a worldwide scale. By way of example, there exist in the art a vibrational viscosity sensor and an acoustic viscosity sensor.

The vibrational viscosity sensor includes a rod, a cylinder and a movable sensor part of a fork or tube shape to vibrate at a resonant frequency. In the vibrational viscosity sensor, a viscosity of fluid acts as a force for damping the vibration. Generally, as the viscosity increases, the amplitude and bandwidth of the damped vibration decrease and increase, respectively. As examples of the vibrational viscosity sensor, a twisting viscometer and a tuning fork viscometer are disclosed in U.S. Pat. Nos. 4,811,593 and 7,043,969, respectively. There are disadvantages in that such vibrational viscometers have a relatively large size and the movable sensor part must be sealed.

The acoustic viscosity sensor has advantages in that it is sized relatively small and does not have a movable sensor part. The acoustic viscosity sensor excites a compression wave, which is referred to as the so-called acoustic wave, into fluid and measures a wave reflecting from the fluid. An example of the acoustic viscosity sensor is disclosed in U.S. Pat. No. 6,439,034. The acoustic viscosity sensor includes an acoustic wave generator, a transmitting piezoelectric transducer, a receiving piezoelectric transducer and a phase-shift detector. The acoustic wave generator, which is in contact with the fluid, is connected to the transmitting piezoelectric transducer. The transmitting piezoelectric transducer serves to transmit a longitudinal wave through the fluid. The longitudinal wave and a shear wave corresponding thereto are detected by the receiving piezoelectric transducer, which is spaced apart from the transmitting piezoelectric transducer and is connected to the phase-shift detector. The phase-shift detector is also connected to the transmitting piezoelectric transducer. The phase-shift detector detects a phase difference between the longitudinal wave transmitted by the transmitting piezoelectric transducer and the shear wave detected by the receiving piezoelectric transducer. The phase difference is used to obtain a velocity of the shear wave and a dynamic viscosity of the fluid. However, the acoustic viscosity sensor has a disadvantage in that the velocity of the shear wave is affected by the viscosity as well as a contaminant such as particles or bubbles in the fluid.

Recently, focus was directed to a viscosity sensor using a surface acoustic wave (SAW). The surface acoustic wave viscosity sensor is smaller than the acoustic viscosity sensor. Further, the surface acoustic wave viscosity sensor without the movable sensor part can conduct an in-situ measurement in a limited place or a poor environment. Especially, since the surface acoustic wave does not emit a large amount of energy into a fluid, it can detect the surface acoustic wave without excessive damping.

A measure principle of the surface acoustic wave viscosity sensor is directed to using the transfer of acoustic shear wave energy from a solid waveguide (e.g., a plate of quartz) having a characteristic material impedance $Z_w=(\rho_w\mu)^{1/2}$ into an adjacent fluid having a characteristic material impedance $Z_L=(\omega\rho_L\eta)^{1/2}$. Herein, $\rho_w$ is a density of the waveguide, $\rho_L$ is a density of the fluid, $\mu$ is a shear elastic modulus of the waveguide, $\omega$ is a radian frequency of the acoustic shear wave, and $\eta$ is a dynamic viscosity of the fluid. An energy transfer is proportional to the ratio $Z_L/Z_w$ under the condition of $Z_L \ll Z_w$. The square root of a power loss is proportional to the product $\omega\rho\eta$ of frequency, density and viscosity. If one knows the frequency, then the viscosity-density product can be measured. Further, although a turbulent flow occurs, the sample fluid remains stationary to ultrasonic vibrations in the quartz crystal regardless of the flow rate of the bulk fluid.

The surface acoustic wave viscosity sensor may be based on one of two modes, one of which wherein the wave propagates through a piezoelectric substrate and the other of which wherein the wave propagates on the piezoelectric substrate. Those modes are determined by a crystal cut of the quartz element. Methods using an acoustic wave in a thickness shear mode are disclosed in U.S. Pat. Nos. 4,741,200 and 5,741,961. Further, devices using a SH-APM (Shear-Horizontal Acoustic Plate Mode) and a FPW (Flexural Plate Wave) are disclosed in U.S. Pat. Nos. 6,304,021 and 7,287,431, respectively.

The surface acoustic wave viscosity sensor is small and has a microchip. However, the surface acoustic wave viscosity sensor is expensive due to expensive materials of the waveguide. Further, a depth $\delta = (\eta/\pi \rho_1 f)^{1/2}$, by which the acoustic wave is transmitted into the fluid in the surface acoustic wave viscosity sensor, is in inverse proportion to the square root of the frequency. Accordingly, there is a problem with the surface acoustic wave viscosity in that it locally responds to a physicochemical property of a minute region existing at an interface between the solid and the liquid.

The surface acoustic wave viscosity sensor operates at a frequency range of 1~200 MHz. Further, when the acoustic wave with high frequency propagates through the fluid having a high molecular weight, a displacement rate of the fluid with the high molecular weight is smaller than a frequency at which the surface acoustic wave viscosity sensor vibrates. Thus, the fluid with the high molecular weight tends to behave like a gel. In such a case, the values measured by the surface acoustic wave viscosity sensor fail to accurately show the physicochemical properties under an actual usage of the fluid. Further, when contaminants exist in the fluid sample or aggressive agents exist in the fluid, particles may adhere on the surface of the surface acoustic wave viscosity sensor to thereby cause a distortion of measured signals. Thus, a sensitivity factor due to the contaminants or the aggressive agents must be considered beforehand. In addition, the surface acoustic wave viscosity sensor must be replaced regularly. Besides, the surface acoustic wave viscosity sensor using a high frequency inevitably has a complicated electronic circuit.

A magnetoelastic viscosity sensor is considered as an alternative to the surface acoustic wave viscosity sensor. The piezoelectric sensor generally uses a capacitive electrode, whereas the magnetoelastic viscosity sensor uses an inductive coil.

Recently, attention has been given to the magnetoelastic viscosity sensor using the inductive coil. The magnetoelastic viscosity sensor uses an amorphous metallic glass (Metglas) ribbon as its key part. The magnetoelastic viscosity sensor utilizes a phenomenon that a magnetoelastic ribbon vibrates in a length direction thereof when applying an alternating magnetic field to the magnetoelastic ribbon. A frequency of the alternating magnetic field is similar to a natural frequency of the magnetoelastic ribbon. The vibration generated from the magnetoelastic ribbon is measured as a voltage by a pick-up coil disposed around the magnetoelastic ribbon. A resonant frequency is proportional to the density and thickness of the magnetoelastic ribbon as well as other boundary conditions between the environment or fluid and a surface of the magnetoelastic ribbon. When a viscous fluid exists around the magnetoelastic ribbon, the resonant frequency is shifted towards lower frequency due to the dissipative character of the shear forces associated with fluid viscosity. The natural frequency may be obtained from the following Equation 1:

$$\Delta f = f_n - f_d = \frac{\sqrt{n f_n}}{2\sqrt{2} \rho_s d}(\eta \rho_L)^{\frac{1}{2}}, \quad \text{Eq. (1)}$$

wherein $\Delta f$ is a frequency shift value, $\rho_s$ is a density of the magnetoelastic ribbon, $\rho_L$ is a density of the fluid, $\eta$ is a dynamic viscosity of the fluid, and d is a thickness of the magnetoelastic ribbon.

That is, the resonant frequency of the magnetoelastic ribbon is proportional to the square root of the product of the viscosity and the density of the fluid. In Equation (1), the effect of the density $\rho_L$, of the fluid on the frequency shift value $\Delta f$ may be similar to that of the aforementioned surface acoustic wave viscosity sensor. Thus, to measure the viscosity of the fluid independently, the density of the fluid must be known beforehand. However, a lubricant oil maintains its density almost constant (negligible change) in spite of a rapid change of the viscosity. Thus, the viscosity of such fluid can be measured immediately.

In this regard, a method of measuring an oil viscosity using the magnetoelastic ribbon is suggested in the following papers: a paper entitled "Magneto-acoustic sensors for measurement of liquid temperature, viscosity and density" (Jain, M. K.; Schmidt, S.; and Grimes, C. A.) published in the *Applied Acoustics*, Volume 62, Issue 8, August 2001, Pages 1001-1011; and a paper entitled "Effect of surface roughness on liquid property measurements using mechanically oscillating sensors" (Jain, M. K.; and Grimes, C. A.) published in the *Sensors and Actuators*, Volume 100, Issue 1, 15 Aug. 2002, Pages 63-69. FIG. 1 schematically shows an arrangement of a magnetoelastic ribbon according to the prior art. In the suggested methods, the magnetoelastic ribbon is located on a bottom of a glass beaker filled with oil. Referring to FIG. 1, the magnetoelastic ribbon 11 is placed on a plexiglas substrate 12. Baffle holes 13 with a diameter of 3 mm are formed in the substrate 12. Supports 14 for supporting the magnetoelastic ribbon 11 are disposed on the substrate 12. That is, the magnetoelastic ribbon 11 is spaced apart from the substrate 12 by the supports 14. Thus, it is possible to prevent the acoustic wave from reflecting again from a back side of the magnetoelastic ribbon 11.

Further, a method of decreasing an over damping, which occurs in a magnetoelastic ribbon when measuring a fluid viscosity using a thick magnetoelastic film sensor, is suggested by a paper entitled "Viscosity measurements of viscous liquids using magnetoelastic thick-film sensors" (Loiselle, K. T.; and Grimes, C. A.) published in the *Review of Scientific Instruments* 2000, Volume 71, Issue 3, Pages 1441-1446. FIG. 2 schematically shows a construction of a magnetoelastic sensor according to the prior art. Referring to FIG. 2, the magnetoelastic sensor 20 includes: a doughnut-shaped boat 21 immersed in an oil; a U-shaped bracket 22 mounted on the boat 21; a magnetoelastic ribbon 23 centrally disposed in the boat 21; and a coil 24 wound around the magnetoelastic ribbon 23. Insofar as a density of the oil remains constant, the magnetoelastic ribbon 23 may be immersed at a constant depth in the oil, although an absolute oil level changes. The magnetoelastic sensor 20 is immersed in the oil at a depth of 2.5 mm and measures a viscosity within a range of 100~1500 cSt.

However, when the magnetoelastic sensor 20 is positioned in an oil tank, the magnetoelastic ribbon may float freely on the oil. Thus, the magnetoelastic sensor 20 cannot measure an accurate viscosity of the oil. Further, a power of an electromagnetic field cannot flow from the magnetoelastic ribbon 23 to the magnetoelastic sensor 20 in iron or ferromagnetic bodies. Accordingly, the magnetoelastic sensor 20 cannot be used in tanks, containers and pipes, which are made from an iron or ferromagnetic material. Furthermore, the magnetoelastic sensor 20 does not conduct measurement of the oil viscosity based on a change in the natural frequency of the magnetoelastic ribbon 23 according to a temperature change.

SUMMARY

According to various aspects, embodiments of a probe for measuring an oil viscosity are provided. In one exemplary embodiment, by way of non-limiting example, the probe includes a housing, a magnetoelastic ribbon, an electromagnetic coil, a temperature sensor and an electrical board. The housing is mounted to a member configured to contain an oil. The magnetoelastic ribbon is fixed to an inside of the housing through a first insert member at least partially immersed in the oil at an opposite end. The electromagnetic coil is disposed in the housing to surround the magnetoelastic ribbon. The temperature sensor is mounted to the housing to measure a temperature of the oil. The electrical board is electrically connected to the electromagnetic coil and the temperature sensor.

A further aspect relates to an apparatus for monitoring an oil viscosity. In one exemplary embodiment, by way of non-limiting example, the apparatus includes a housing, a viscosity sensor, a temperature sensor, an electrical board and an electronic module. The housing is mounted to a member configured to contain an oil. The viscosity sensor includes a magnetoelastic ribbon and an electromagnetic coil. The temperature sensor is mounted to the housing for measuring a temperature of the oil. The electrical board is electrically connected to the viscosity sensor and the temperature sensor. The electronic module is electrically connected to the electrical board. One end of the magnetoelastic ribbon is fixed to the inner side of the housing through a first insert member, while the opposite end of the magnetoelastic is at least partially immersed in the oil. The electromagnetic coil is disposed in the housing to surround the magnetoelastic ribbon.

A further aspect of the present invention relates to a method of monitoring an oil viscosity. According to an exemplary embodiment of the method, an oil viscosity probe having a magnetoelastic ribbon and an electromagnetic coil is positioned in an oil. A DC bias voltage and an AC excitation voltage are applied to the electromagnetic coil. A signal $S_{oil}$ induced in the electromagnetic coil is measured while shutting off the AC excitation voltage. A temperature T of the oil is measured. A natural frequency $f_{n\_oil}(T)$ of the magnetoelastic ribbon is estimated in the oil at the temperature T based on the signal $S_{oil}$ analysis. A natural frequency $f_{n\_air}(T)$ of the magnetoelastic ribbon is estimated in the air at the temperature T. A difference $\Delta f$ in the natural frequencies $f_{n\_oil}(T)$, $f_{n\_air}(T)$ of the magnetoelastic ribbon is calculated. An acoustic viscosity AV, a kinematic viscosity $\nu$ and a dynamic viscosity $\eta$ are calculated.

This summary is provided to introduce a selection of concepts in a simplified form that are further described below in the detailed description. This summary is not intended to identify key features or essential features of the claimed subject matter, nor is it intended to be used to determine the scope of the claimed subject matter.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. One of ordinary skill in the art may realize that the following description is illustrative only and is not in any way limiting. Other illustrative embodiments may readily suggest themselves to such skilled persons having the benefit of this disclosure.

Figure 1:
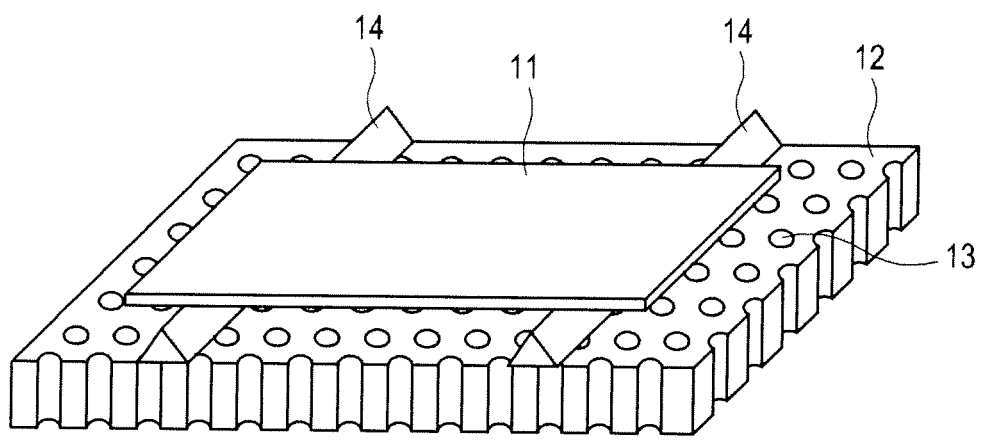
FIG. 1 is a perspective view schematically showing an arrangement of a magnetoelastic ribbon according to the prior art.
Figure 2:
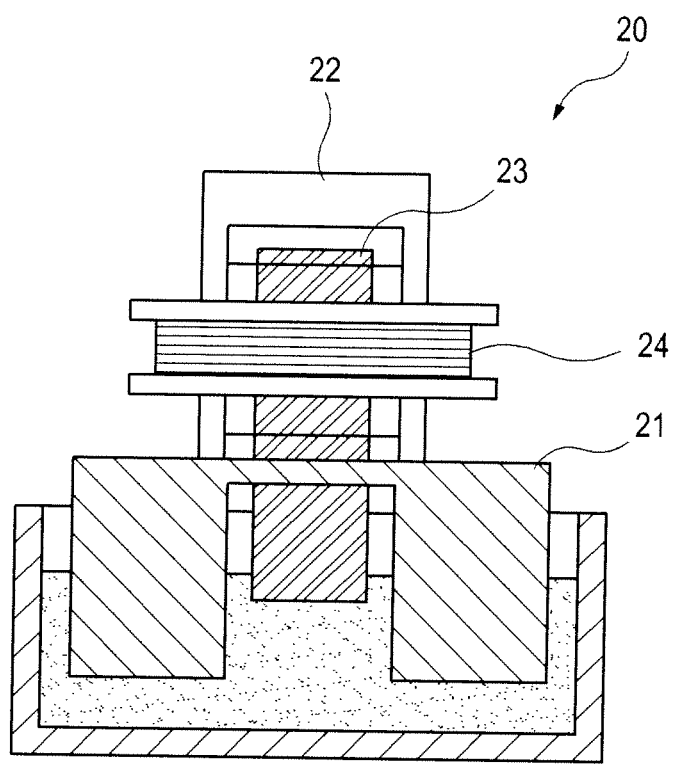
FIG. 2 schematically shows a construction of a magnetoelastic sensor according to the prior art.
Figure 3:
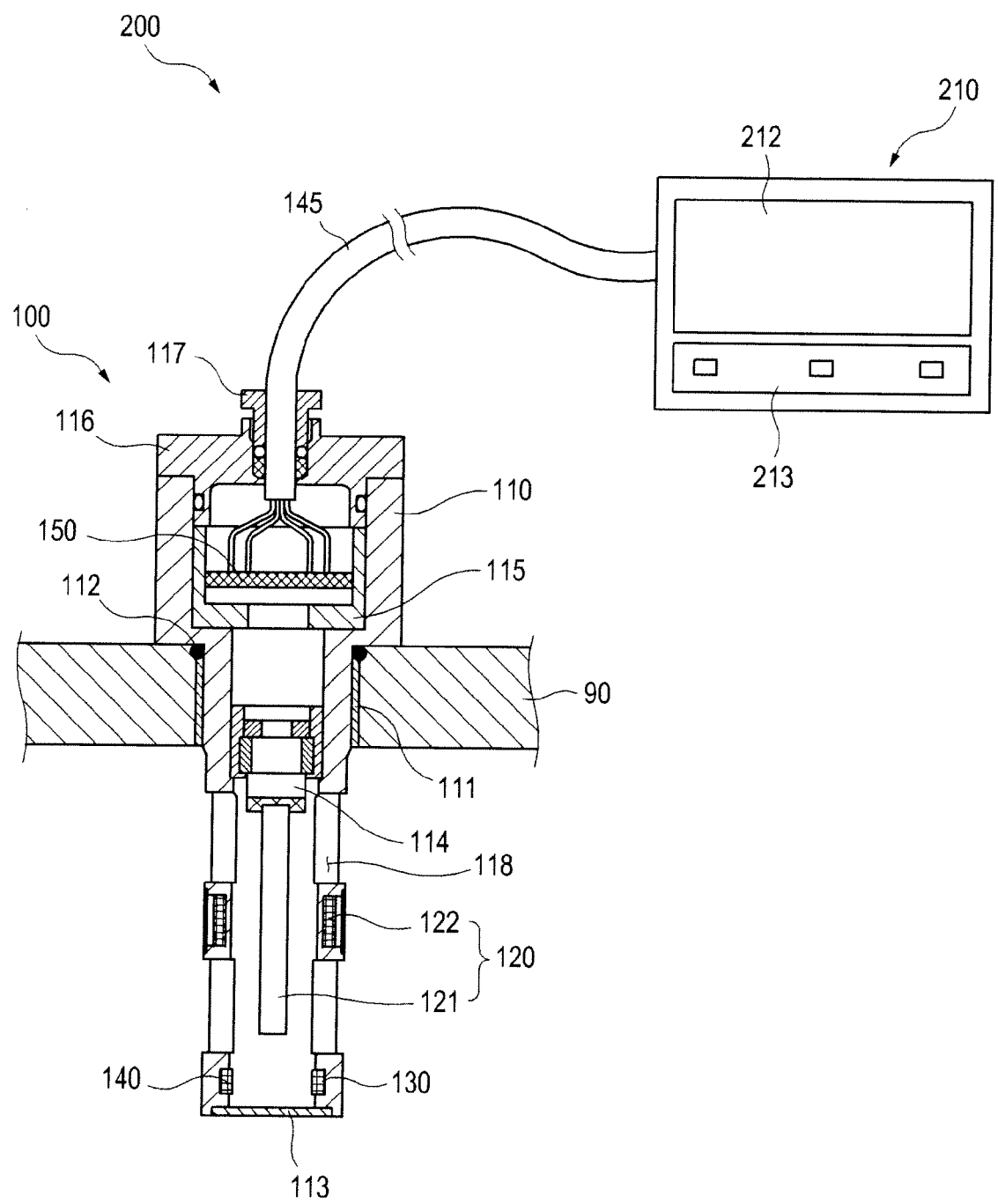
FIG. 3 shows an apparatus for monitoring an oil viscosity according to one embodiment of the present invention.

Referring to FIG. 3, a probe for measuring an oil viscosity 100 (hereinafter referred to as "oil viscosity probe") according to one embodiment includes a housing 110, a viscosity sensor 120, a temperature sensor 130, a moisture sensor 140 and an electrical board 150.

Further referring to FIG. 3, an apparatus for monitoring an oil viscosity 200 (hereinafter referred to as "oil viscosity monitoring apparatus") according to one embodiment includes the oil viscosity probe 100 and an electronic module 210.

The housing 110 is mounted to an oil containing member 90 for containing or storing oil such as a tank, a container, a pipe, a tube, etc. The housing 110 is made from a nonmagnetic material and has a hollow cylindrical shape. One end of the housing 110 is open and the housing 110 being formed with at least one port 118 sized to allow oil within the oil container to enter into the cylindrical portion of the housing 118. Thus, when the housing 110 is immersed in the oil, the oil enters an inside of the housing 110. A magnetoelastic ribbon 121 is fixed to the inside of the housing 110 and an electromagnetic coil 122 is disposed in the housing 110 to surround the magnetoelastic ribbon 121. The housing 110 may be configured to thread-engage to the oil containing member 90. To this end, threads 111 are formed on a peripheral surface of the housing 110. Thus, the oil viscosity probe 100 may be easily coupled to or separated from the oil containing member 90. Further, an O-ring 112 is disposed between the threads 111 and the oil containing member 90 for ensuring seal therebetween. Further, a protective mesh 113 is attached to the one end of the housing 110. The protective mesh 113 serves to prevent mechanical damages on the magnetoelastic ribbon 121 and further prevent air bubbles in the oil from approaching the magnetoelastic ribbon 121.

The viscosity sensor 120 comprises the magnetoelastic ribbon 121 and the electromagnetic coil 122. One end of the magnetoelastic ribbon 121 is fixed to the inside of the housing 110 through a first insert member 114, while an opposite end of the magnetoelastic ribbon 121 is at least partially immersed in the oil. The magnetoelastic ribbon 121 may comprise a ferrous alloy material (e.g., Fe40Ni38Mo4B18 alloy). The electromagnetic coil 122 is wound around the magnetoelastic ribbon 121 in the housing 110. Further, the electromagnetic coil 122 is embedded to the housing 110 so as not to contact the oil. The electromagnetic coil 122 is electrically connected to the electrical board 150.

The temperature sensor 130 is coupled or fitted to the one end of the housing 110 so as to measure the oil temperature in a contact or non-contact manner. The temperature sensor 130 may include a platinum thermocouple. Thus, with the temperature sensor 130, the oil viscosity of the oil can be more accurately measured in view of the natural frequency of the magnetoelastic ribbon 121 according to the change in the oil temperature.

The moisture sensor 140 for measuring moisture contained within the oil (i.e., moisture contents) is coupled or fitted to the one end of the housing 110 and electrically connected to the electrical board 150. The moisture sensor is configured to monitor an effect of the moisture contents on the oil viscosity. Generally, air hygrometers include a semiconductor chip having thermosetting resins, three capacitance layers and platinum electrodes. However, the thermosetting resins are not applicable to the oil. Thus, to cope with such a problem, the thermosetting resin is coated with an oleophobic coating. For example, a fluorosilane polymer, which is dissolved in a transparent hydrofluoroether solvent with low viscosity, is used as the oleophobic coating.

The electric board 150 is fixed to an opposite end of the housing 110 through a second insert member 115 and a cover 116. The electrical board 150 may include a printed circuit board or any other circuit board with electric or electronic elements mounted thereon. The electrical board 150 is electrically connected to the electronic module 210 via a cable 145. A bushing 117 is fitted between the cable 145 and the cover 116 for seal therebetween. The electrical board 150 is electrically connected to the viscosity sensor 120. If an AC voltage and a DC voltage are applied from the electrical board 150 to the electromagnetic coil 122 of the viscosity sensor 120, then the magnetoelastic ribbon 121 vibrates. If the electrical board 150 shuts off the AC voltage applied to the electromagnetic coil 122, then the vibration of the magnetoelastic ribbon 121 induces an induced voltage in the electromagnetic coil 122, thereby generating a signal based on the induced voltage. The electrical board 150 receives the signal outputted from the electromagnetic coil 122. Further, the electrical board 150 is electrically connected to the temperature sensor 130 and the moisture sensor 140. The electrical board 150 serves to supply an electrical power to those sensors and receive measured signals from those sensors.

Figure 4:
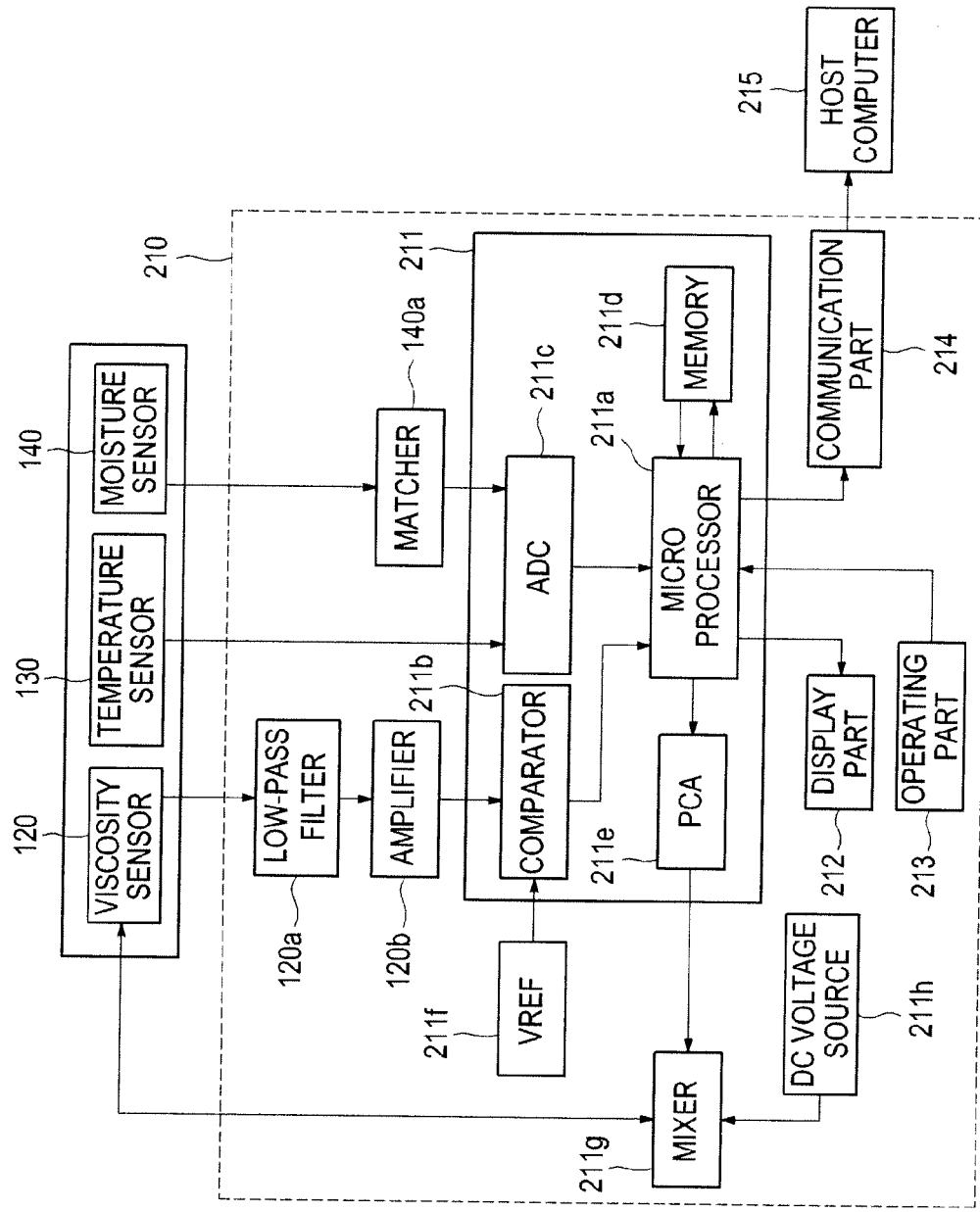
FIG. 4 is a block diagram showing a configuration of the apparatus for monitoring the oil viscosity of FIG. 3.

Referring to FIGS. 3 and 4, the electronic module 210 may include a control part 211, a display part 212 and an operating part 213. The electronic module 210 is electrically connected to the electrical board 150. The control part 211 controls each of the sensors (e.g., the viscosity sensor 120, the temperature sensor 130 and the moisture sensor 140) electrically connected to the electrical board 150 and processes the signals received from each of the sensors. The display part 212 displays values processed by the control part 211. The operating part 213 may include buttons or switches for operating the control part 211.

The control part 211 may include the following: a microprocessor 211a; a comparator 211b; an analog-to-digital converter (ADC) 211c; a memory 211d; a programmable counter array (PCA) 211e; reference voltages (VREF) 211f; a mixer 211g; and a DC voltage source 211h.

A signal, which is outputted from the viscosity sensor 120, is sent to the control part 211 through a low-pass filter 120a and then an amplifier 120b. The signal, which is amplified by the amplifier 120b, is sent to the microprocessor 211a through the comparator 211b. The comparator 211b compares the pre-stored VREF 211f with measured values.

An analog signal, which is outputted from the temperature sensor 130, is converted to a digital signal through the ADC 211c and then sent to the microprocessor 211a. An analog signal, which is outputted from the moisture sensor 140, is matched through the matcher 140a and is then converted to a digital signal through the ADC 211c and is thereafter sent to the microprocessor 211a.

The microprocessor 211a sends an AC excitation voltage to the mixer 211g through the PCA 211e. The mixer 211g mixes the AC excitation voltage and a DC bias voltage received from the DC voltage source 211h and sends the mixed voltages to the viscosity sensor 120.

The microprocessor 211a outputs calculated viscosity values through the display part 212. The display part 212 may include a liquid crystal display (LCD) and a status indicator. As for the LCD, the LCD may display the viscosity value in numerical characters. As for the status indicator, the status indicator may indicate the viscosity values as a result of comparison between the viscosity value and predetermined threshold values. For example, the status indicator may have light emitting diodes (LEDs) that flicker in green, yellow and red according to "NORMAL", "WARNING" and "DANGER" statuses respectively.

The operating part 213 generates a signal for loading data from the memory 211d through the microprocessor 211a or for storing data in the memory 211d. Further, the operating part 213 may generate a signal for resetting the electronic module 210.

The electronic module 210 may further include a communication system 214 for communicating with a host computer 215. The communication system 214 may include wired or wireless communication hardware to send and receive data and commands between the control part 211 and the host computer 215.

Figure 5:
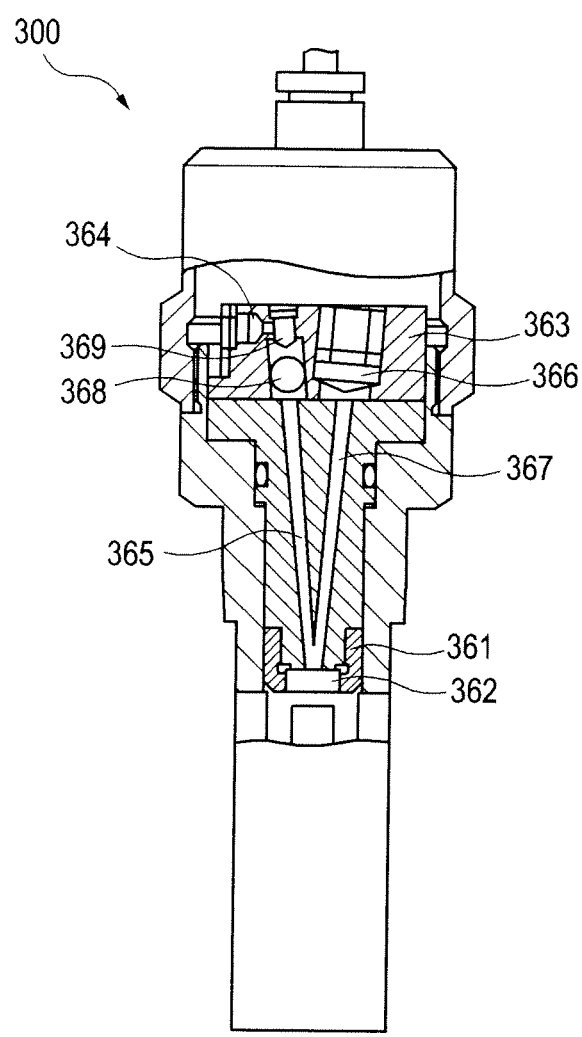
FIG. 5 is a partially sectioned view showing an oil viscosity probe according to another embodiment of the present invention.

In another embodiment, the oil viscosity probe may include an oxidation sensor that measures an oil oxidation by measuring a fluorescence of the oil. FIG. 5 shows such an oil viscosity probe and FIG. 6 shows an oil monitoring apparatus including the same.

Figure 6:
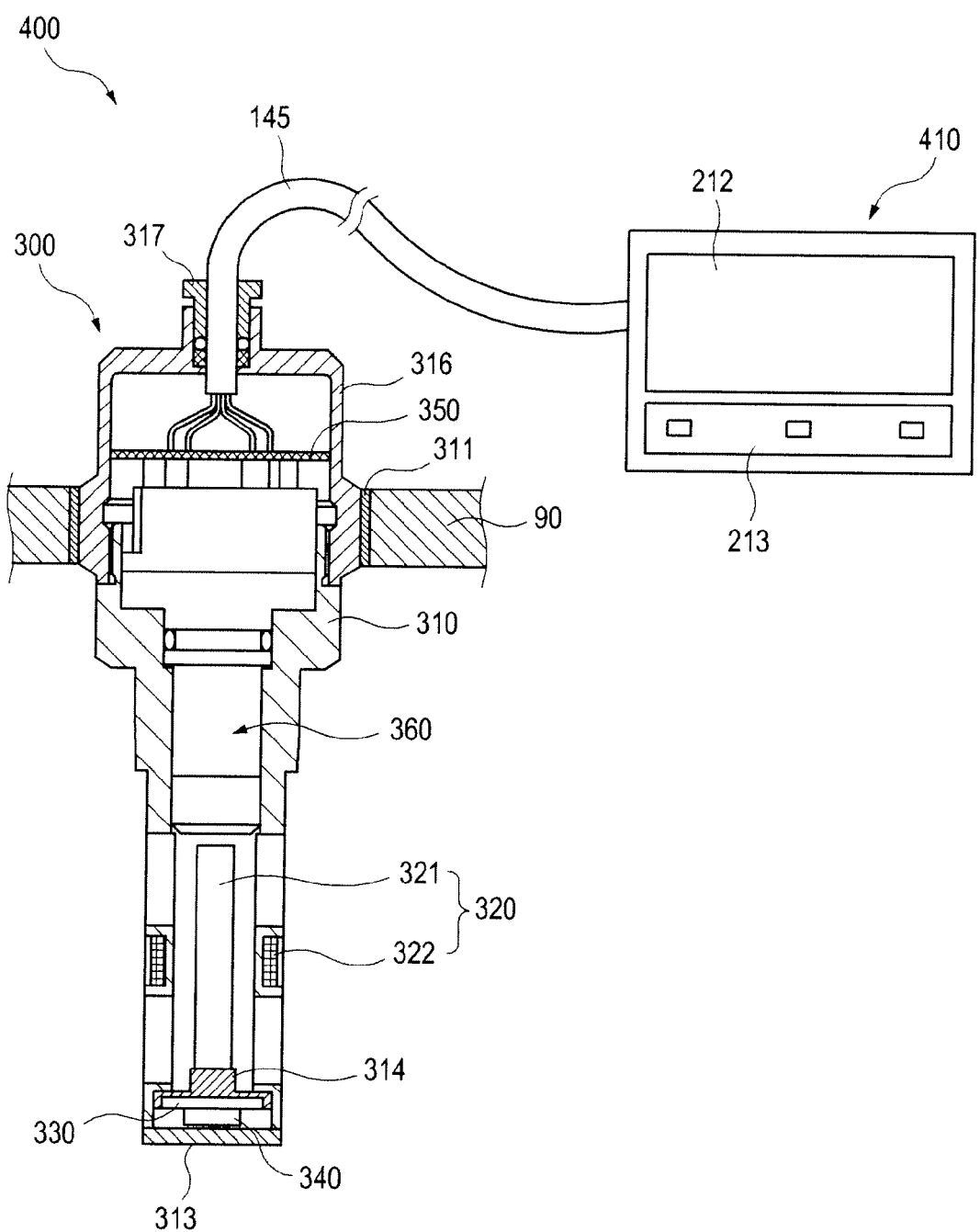
FIG. 6 shows an apparatus for monitoring an oil viscosity according to another embodiment of the present invention.

Referring to FIGS. 5 and 6, the oil viscosity probe 300 constructed according to another embodiment includes a housing 310, a viscosity sensor 320, a temperature sensor 330, a moisture sensor 340, an electrical board 350 and an oxidation sensor 360.

The oxidation sensor 360 measures the oil oxidation by measuring a fluorescence of the oil. The oxidation sensor 360 is electrically connected to the electrical board 350. By way of an example, the oxidation sensor may be configured similar to an oil oxidation sensor suggested in U.S. Pat. No. 7,391,035.

Referring to FIG. 5, the oxidation sensor 360 may include a holder 361, a transparent optical window 362, an ultraviolet light emitting diode 364, a first optical fiber 365, a color sensor 366 and a second optical fiber 367. The transparent optical window 362 is coupled to the holder 361 to be in contact with the oil. The ultraviolet light emitting diode 364 is coupled to a bushing 363 to irradiate an ultraviolet light. The first optical fiber 365 extends from the ultraviolet light emitting diode 364 toward the oil. The color sensor 366 is coupled to the bushing 363. The second optical fiber 367 extends from the color sensor 366 toward the oil. The ultraviolet light, which is emitted from the ultraviolet light emitting diode, is irradiated into the oil through the transparent optical window 362 and the first optical fiber 365. In order to focus the ultraviolet light emitted from the ultraviolet light emitting diode 364 to the end portion of the first optical fiber 365, a ball lens 368 is provided between the ultraviolet light emitting diode 364 and the end portion of the first optical fiber 365. A fluorescence, which is emitted from the oil and passes through the transparent optical window 362, enters the color sensor 366 through the second optical fiber 367. The oxidation sensor 360 may further comprise a photo diode 369 for stabilizing a light emission of the ultraviolet light emitting diode 364. The color sensor 366 detects the fluorescence intensity in three wavelength bands such as red, green and blue wavelength bands. As shown in following Equation 2, a fluorescence emission ratio (FER) is defined as the ratio of a fluorescence intensity $F_{long}$ in a relatively long wavelength band to a fluorescence intensity $F_{short}$ in a relatively short wavelength band.

$$FER = \frac{F_{long}}{F_{short}} \qquad \text{Eq. (2)}$$

Since the fluorescence emission ratio is associated with a total acid number (TAN), the fluorescence emission ratio can provide information on the oil oxidation.

Referring to FIG. 6, the viscosity sensor 320, the temperature sensor 330, the moisture sensor 340, the electrical board 350 and the oxidation sensor 360 are mounted or fitted to the housing 310. The housing 310 has an open one end, to which a protective mesh 313 is attached. The housing 310 may be configured to thread-engage to the oil containing member 90. To this end, threads 311 are formed on a peripheral surface of the housing 310. Thus, the oil viscosity probe 300 may be easily coupled to or separated from the oil containing member 90. The viscosity sensor 320 includes a magnetoelastic ribbon 321 fixed to the one end of the housing 310 through a first insert member 314 at its one end and an electromagnetic coil 322 disposed in the housing 310 to surround the magnetoelastic ribbon 321. The electrical board 350 is fixed to the housing 310 through a cover 316 without any insert member. A bushing 317 is disposed between the cover 316 and the cable 145 for sealing therebetween. The temperature sensor 330 and the moisture sensor 340 are mounted to the one end of the housing 310 opposite to the first insert member 314. The housing 310, the viscosity sensor 320, the temperature sensor 330, the moisture sensor 340 and the electrical board 350, which are provided in the oil viscosity probe 300 according to this embodiment, may be configured and operate identically or similarly to those of the probe 100 according to the foregoing embodiment, except for difference in shape or arrangement therebetween. Thus, descriptions on the same configuration between those elements are omitted herein.

An oil viscosity monitoring apparatus 400 according to another embodiment may include the above-described oil viscosity probe 300 and an electronic module 410. The electronic module 410 may have the same configuration as the above-described electronic module 210. The oxidation sensor 360 may send signals associated with measured values to the microprocessor of the electronic module 410 and be controlled by the microprocessor.

Next, descriptions will be provided below on a method of monitoring an oil viscosity (hereinafter, referred to as "oil viscosity monitoring method") using, for example, the oil viscosity probes 100, 300 and the oil viscosity monitoring apparatus 200, 400.

Figure 7:
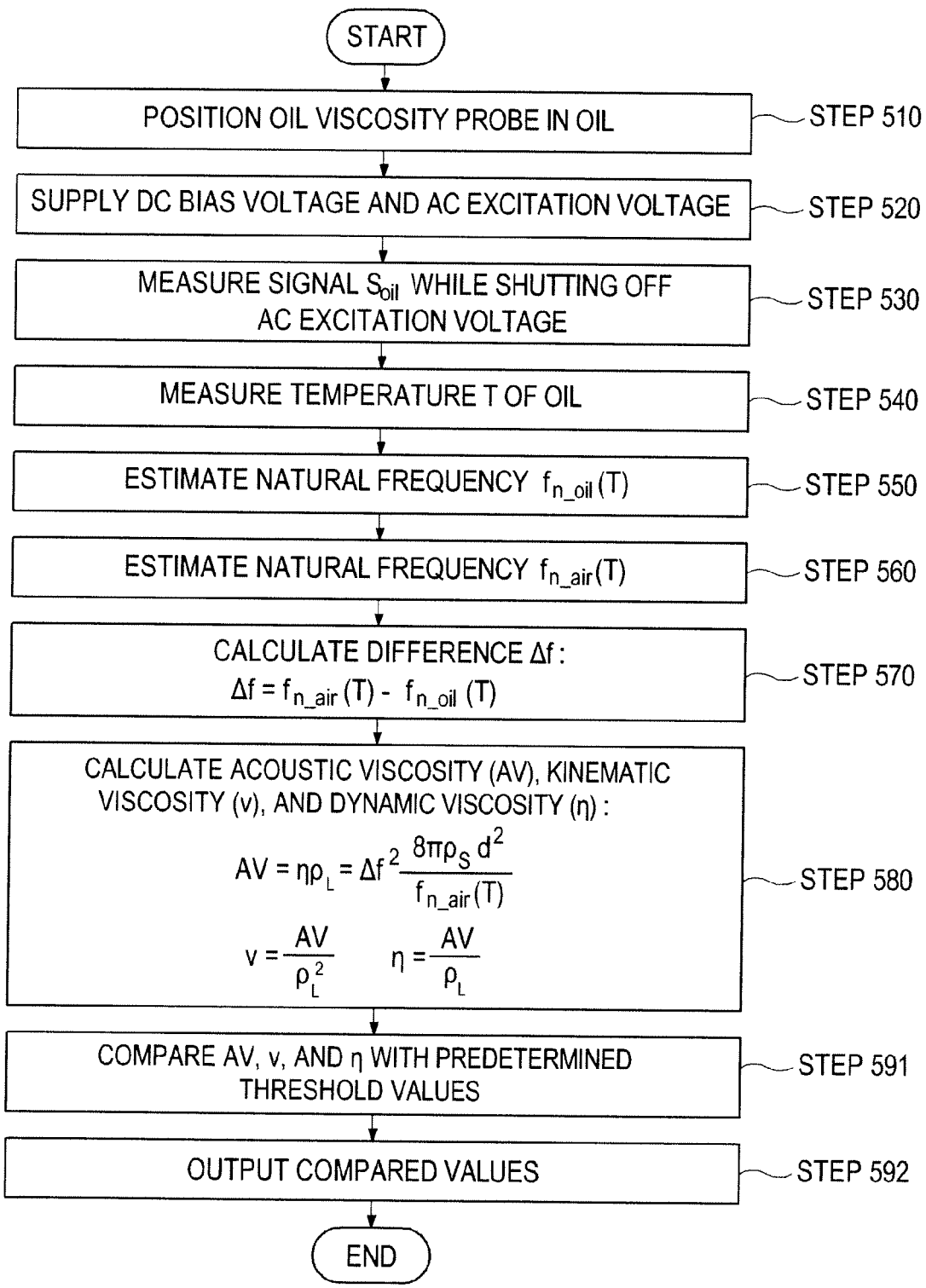
FIG. 7 is a flow chart showing a method of monitoring an oil viscosity according to one embodiment of the present invention.

Referring to FIG. 7, the oil viscosity monitoring method according to one embodiment may comprise the following steps: positioning an oil viscosity probe in an oil (Step 510), the oil viscosity probe having a magnetoelastic ribbon and an electromagnetic coil; supplying a DC bias voltage and an AC excitation voltage to the electromagnetic coil (Step 520); measuring a signal $S_{oil}$ induced in the electromagnetic coil while shutting off the AC excitation voltage (Step 530); measuring a temperature T of the oil (Step 540); estimating a natural frequency $f_{n\_oil}(T)$ of the magnetoelastic ribbon based on the signal $S_{oil}$ in the oil at the temperature T (Step 550); estimating a natural frequency $f_{n\_air}(T)$ of the magnetoelastic ribbon in the air at the temperature T (Step 560); calculating a difference $\Delta f$ between the natural frequencies $f_{n\_air}(T)$, $f_{n\_oil}(T)$ of the magnetoelastic ribbon (Step 570); calculating an acoustic viscosity AV, a kinematic viscosity $\nu$ and a dynamic viscosity $\eta$ (Step 580); comparing the acoustic viscosity AV, the kinematic viscosity $\nu$ and the dynamic viscosity $\eta$ with predetermined threshold values (Step 591); and outputting the compared values (Step 592).

In Step 510, the viscosity sensor 100, 300 having the electromagnetic coil 122, 322 and the magnetoelastic ribbon 121, 321 is positioned in the oil such that the magnetoelastic ribbon 121, 321 is immersed in the oil.

In Step 520, the DC bias voltage and the AC excitation voltage are mixed and then applied to the electromagnetic coil 121, 321. By mixing the DC bias voltage and the AC excitation voltage, it is possible to optimize a performance of the magnetoelastic ribbon 121, 321. If the mixed voltages are supplied to the electromagnetic coil 122, 322, then the magnetoelastic ribbon 121, 321 forcibly vibrates due to an electromagnetic field generated from the electromagnetic coil. The AC excitation voltage is controlled in a range of excitation frequencies ($f_{max}$~$f_{min}$) through the PCA 211e shown in FIG. 4. The excitation frequencies ($f_{max}$ and $f_{min}$) may be determined in view of a geometric structure of the magnetoelastic ribbon 121, 321 and a natural frequency caused by a material characteristics thereof. For example, when the magnetoelastic ribbon is an annealed 2826 MB with 37 mm (length)×6 mm (width)×0.027 mm (thickness), $f_{max}$ is 36 kHz and $f_{min}$ is 19 kHz.

In Step 530, the signal $S_{oil}$, which is induced in the electromagnetic coil while shutting off the AC excitation voltage applied to the electromagnetic coil 122, 322, is measured. If the AC excitation voltage is shut off, the magnetoelastic ribbon 121, 321 performs a damped vibration by friction to the oil. The signal $S_{oil}$ of the induced voltage is generated from the electromagnetic coil due to the damped vibration of the magnetoelastic ribbon. The signal $S_{oil}$ is sent to the comparator 211b through the low pass filter 120a and the amplifier 120b. The comparator 211b compares the signal $S_{oil}$ with the VREF 211f and outputs a high level (the signal $S_{oil}$ is higher than the VREF 2110 or a low level (the signal $S_{oil}$ is lower than the VREF 211f) and sends such a result to the microprocessor 211a.

In Step 540, the temperature T of the oil is measured in order to compensate the change in natural frequency of the magnetoelastic ribbon 121, 321 according to the change of the oil temperature.

In Step 550, the microprocessor 211a estimates the natural frequency $f_{n\_oil}(T)$ of the magnetoelastic ribbon 121, 321 in the oil based on transitions of comparator output from the high level and the low level which are received from the comparator 211b. A response pulse period $\tau_r$ is calculated by following Equation 3:

$$\tau_r = \frac{t_{accum}}{N}. \quad \text{Eq. (3)}$$

wherein N is number of pulses and $t_{accum}$ is a time when the response pulses are accumulated during N pulses.

A difference $\Delta\tau$ between the response pulse period $\tau_r$ and an excitation pulse period $\tau_{exc}$ is defined as following Equation 4:

$$\Delta\tau = \tau_r - \tau_{exc} \quad \text{Eq. (4).}$$

The response pulse period $\tau_r$ can be found by changing the excitation pulse period $\tau_{exc}$ so as to minimize the difference $\Delta\tau$.

The natural frequency $f_{n\_oil}(T)$ of the magnetoelastic ribbon 121, 321 in the oil is estimated by following Equation 5:

$$f_{n\_oil}(T) = \frac{1}{\tau_r}. \quad \text{Eq. (5)}$$

In Step 560, the natural frequency $f_{n\_air}(T)$ of the magnetoelastic ribbon 121, 321 is estimated in the air at the temperature T that is measured in Step 540.

Figure 8:
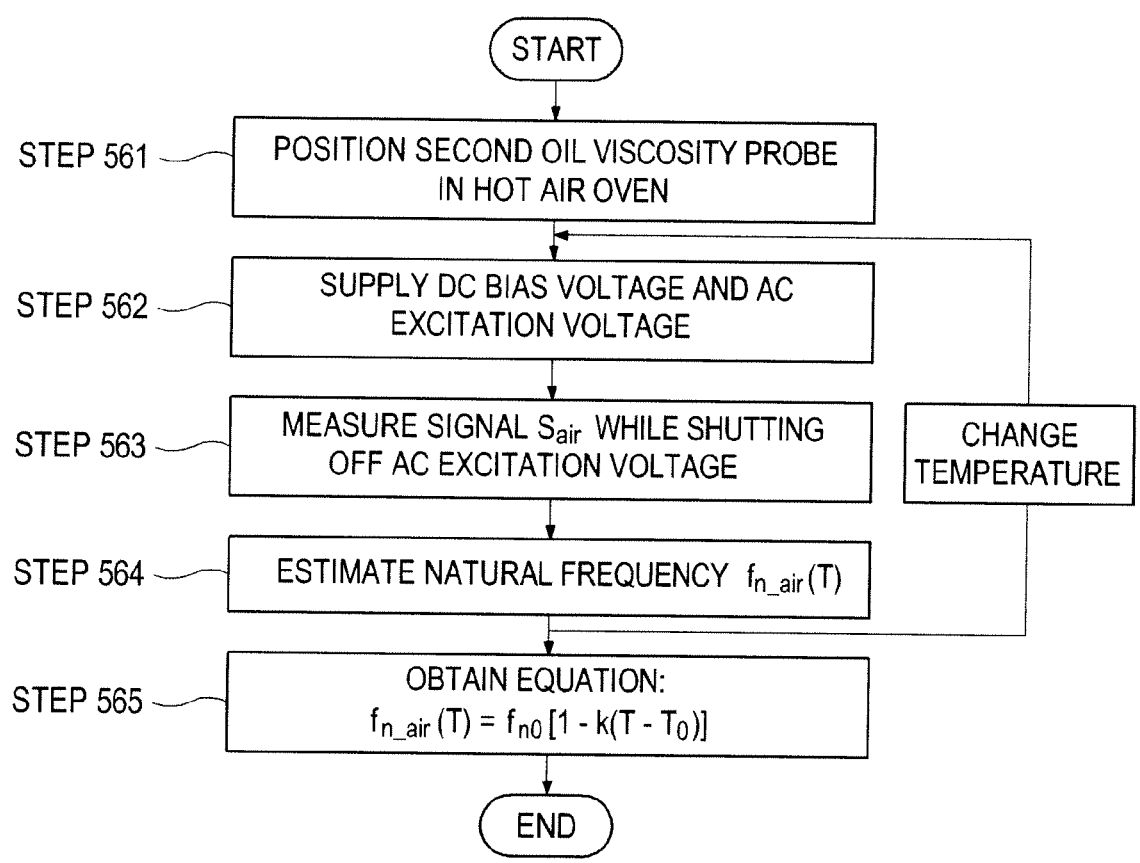
FIG. 8 is a flow chart showing a method of measuring temperature dependence of a natural frequency in air according to one embodiment of the present invention.

Referring to FIG. 8, said Step 560 may comprises the following steps: positioning a second oil viscosity probe in a hot air oven at the temperature T (Step 561), the second oil viscosity probe having a second magnetoelastic ribbon and a second electromagnetic coil; supplying a DC bias voltage and an AC excitation voltage to a second electromagnetic coil (Step 562); measuring a signal $S_{air}$ induced in the second electromagnetic coil while shutting off the AC excitation voltage (Step 563); and estimating a natural frequency $f_{n\_air}$ (T) of the second magnetoelastic ribbon based on the signal $S_{air}$ analysis (Step 564). Step 562, Step 563 and Step 564 are performed in the similar manner as Step 520, Step 530 and Step 540, respectively.

In Step 560, following Equation 6 is obtained by repeating Steps 562, 563, 564 while changing the temperature in the hot air oven:

$$f_{n\_air}(T) = f_{n0}[1 - k(T - T_0)] \quad \text{Eq. (6).}$$

wherein $f_{n0}$ is a natural frequency at a certain temperature $T_0$ and k is a proportional coefficient.

The proportional coefficient k is determined by a geometric structure and material characteristics of the magnetoelastic ribbon.

As another example, the natural frequency data of the magnetoelastic ribbon according to the air temperature may be stored in the memory 211d. In this case, Step 560 may load the natural frequency data of the magnetoelastic ribbon in the air at the temperature T.

In Step 570, a difference in natural frequency $\Delta f$ of the magnetoelastic ribbon in the oil and the air at the temperature T is calculated by following Equation 7:

$$\Delta f_{n\_air}(T) - f_{n\_oil}(T) \quad \text{Eq. (7).}$$

In Step 580, an acoustic viscosity AV, a kinematic viscosity $\nu$ and a dynamic viscosity $\eta$ are calculated by following Equations 8~10:

$$AV = \eta \rho_L = \Delta f^2 \frac{8\pi \rho_s d^2}{f_{n\_air}(T)}; \quad \text{Eq. (8)}$$

$$\nu = \frac{AV}{\rho_L^2}; \quad \text{Eq. (9)}$$

$$\eta = \frac{AV}{\rho_L}; \quad \text{Eq. (10)}$$

wherein $\rho_s$ is a density of the magnetoelastic ribbon and d is a thickness of magnetoelastic ribbon and $\rho_L$ is a density of the oil.

In Step 591, the comparator 211b judges whether the acoustic viscosity AV, the kinematic viscosity $\nu$ and the dynamic viscosity $\eta$ are lower than first threshold values, or higher than second threshold values or between the first threshold values and the second threshold values. In Step 592, the compared values are displayed through the display part 212. If the acoustic viscosity AV, the kinematic viscosity $\nu$ and the dynamic viscosity $\eta$ are lower than the first threshold values, a signal "NORMAL" is displayed through the display part 212. If the acoustic viscosity AV, the kinematic viscosity $\nu$ and the dynamic viscosity $\eta$ are higher than the first threshold values and lower than the second threshold values (e.g., between the first threshold values and the second threshold values), a signal "WARNING" is displayed through the display part 212. If the acoustic viscosity AV, the kinematic viscosity $\nu$ and the dynamic viscosity r are higher than the second threshold values, a signal "DANGER" is displayed through the display part 212.

Figure 9:
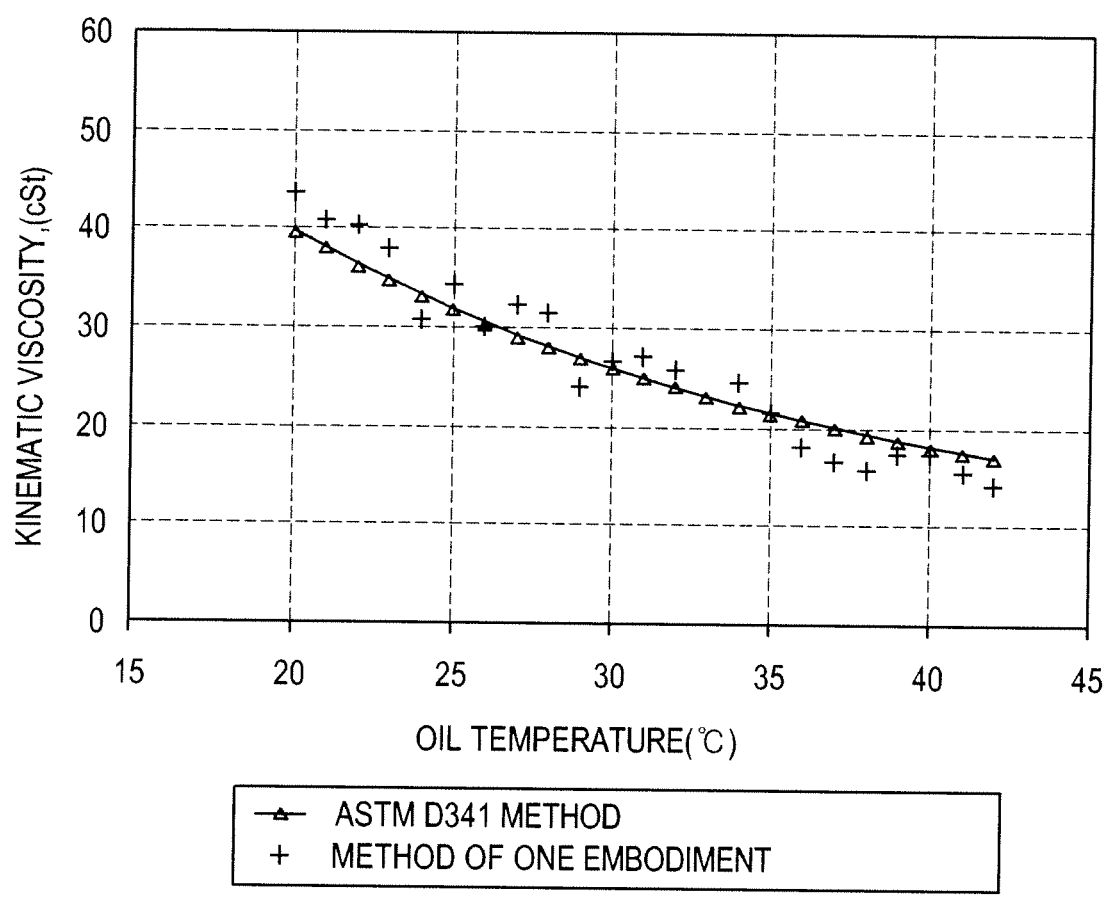
FIG. 9 is a graph showing a temperature dependence of kinematic viscosities, which is calculated by an ASTM (American Society of Testing Materials) D341 method and measured by a method of the present invention from a low viscous synthetic oil sample (PAO#4)
Figure 10:
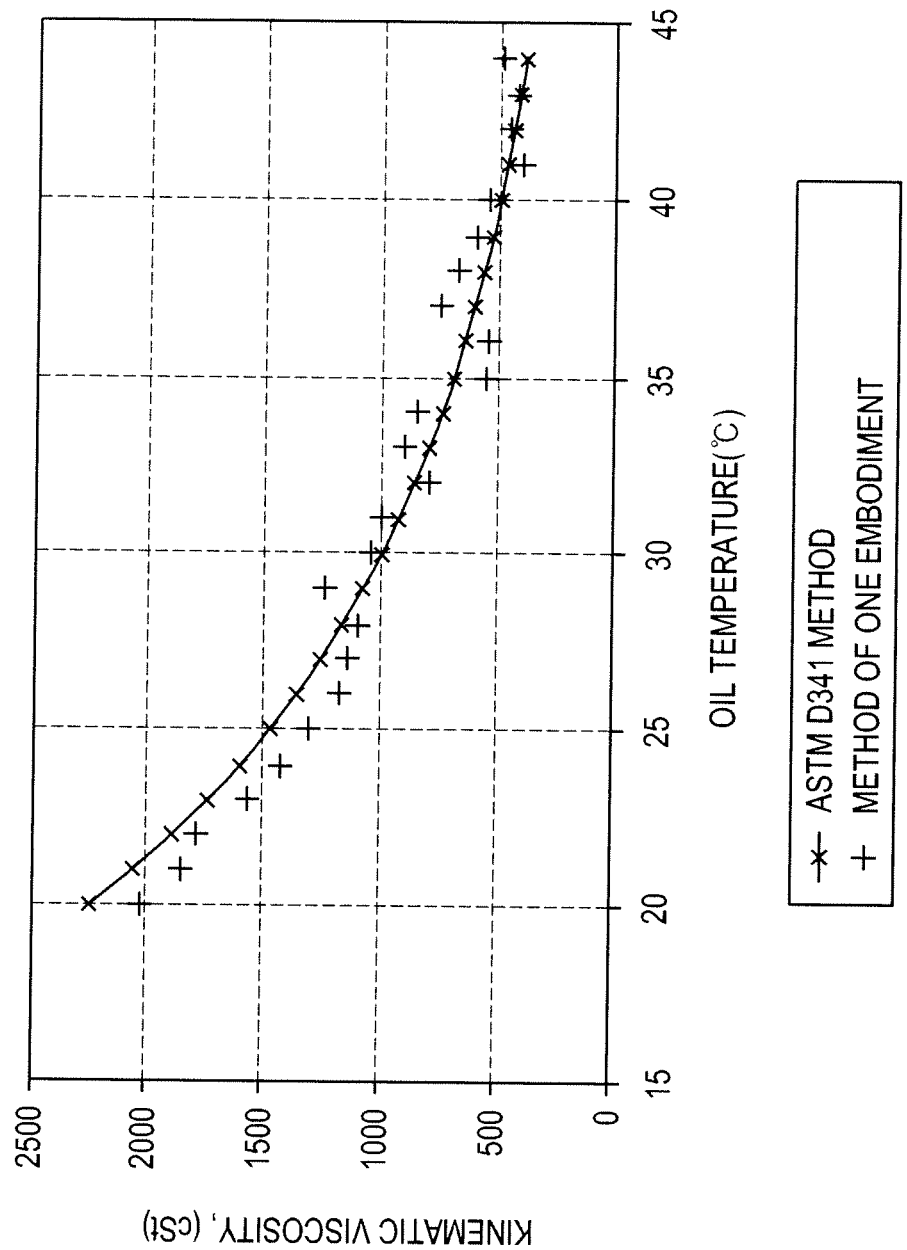
FIG. 10 is a graph showing a temperature dependence of kinematic viscosities, which is calculated by the ASTM D341 method and measured by the method of the present invention from a high viscous mineral oil sample (P-480)

FIGS. 9 and 10 are graphs showing a temperature dependence of kinematic viscosities which are calculated by an ASTM D341 method and measured from a low viscous synthetic oil sample (PAO#4) and a high viscous mineral oil sample (P-480) by means of and measured by a method according to one embodiment. FIGS. 9 and 10 show that the oil viscosity changes depending upon the temperature in a usage environment. As shown in FIGS. 9 and 10, the temperature dependence of the kinematic viscosities, which is measured by means of the method according to one embodiment, is generally equal to that calculated from the ASTM method. Accordingly, it can be ascertained that the kinematic viscosity obtained by the method according to one embodiment is reliable.

Figure 11:
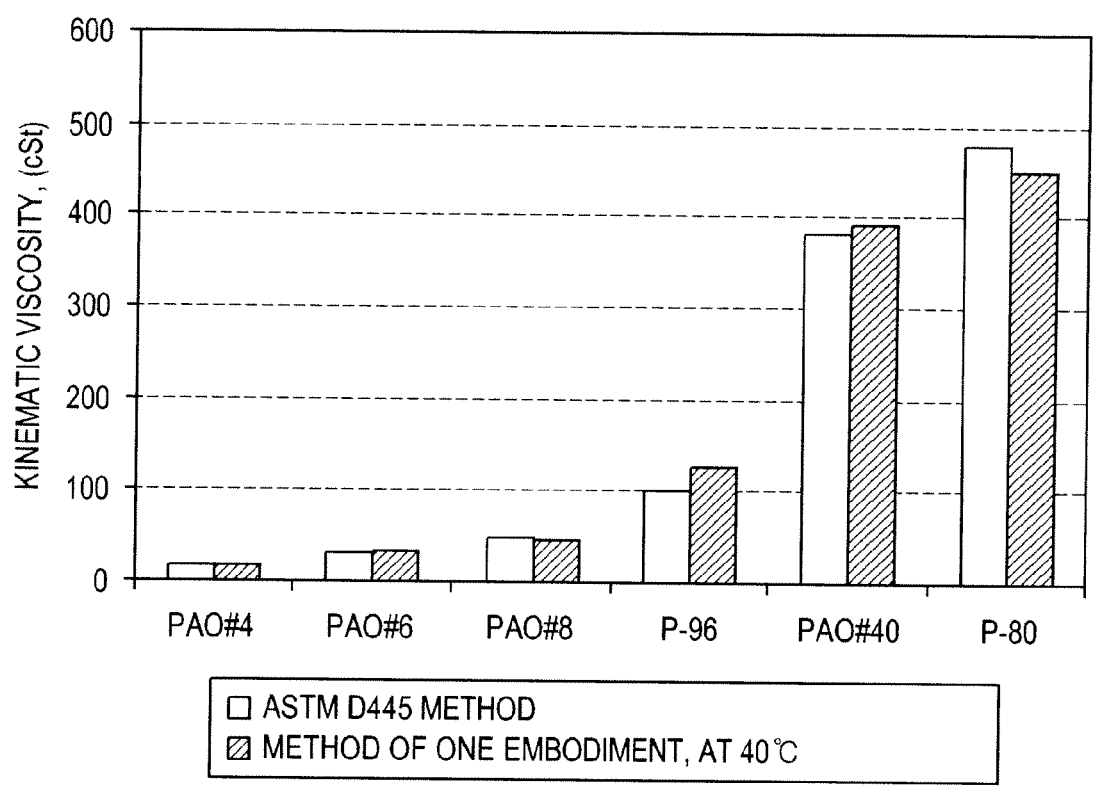
FIG. 11 is a graph showing kinematic viscosities, which are calculated by an ASTM D445 method and measured by the method of the present invention from different types of oil samples at 40° C.
Figure 12:
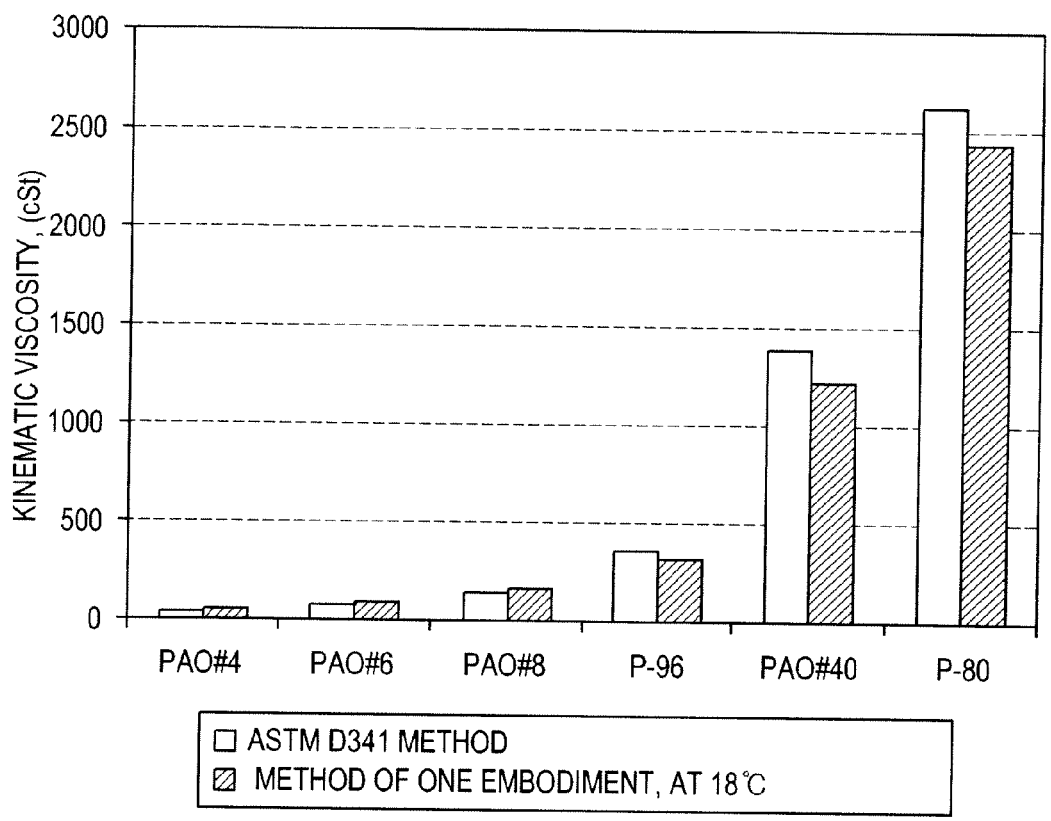
FIG. 12 is a graph showing kinematic viscosities, which are calculated by the ASTM D341 method and measured by the method of the present invention from different types of oil samples at 18° C.

FIG. 11 is a graph showing kinematic viscosities which are calculated by means of an ASTM D445 method and measured by the method according to one embodiment from different kinds of oil samples at 40° C. FIG. 12 is a graph showing kinematic viscosities which are calculated by an ASTM D341 method and measured by the method according to one embodiment from different kinds of oil samples at 18° C. FIGS. 11 and 12 show that the kinematic viscosity measured by means of the method according to one embodiment is generally equal to that estimated by the ASTM methods. Accordingly, it can be ascertained that the kinematic viscosity can be successfully measured within a range of 15~2500 cSt through the method according to one embodiment.

Figure 13:
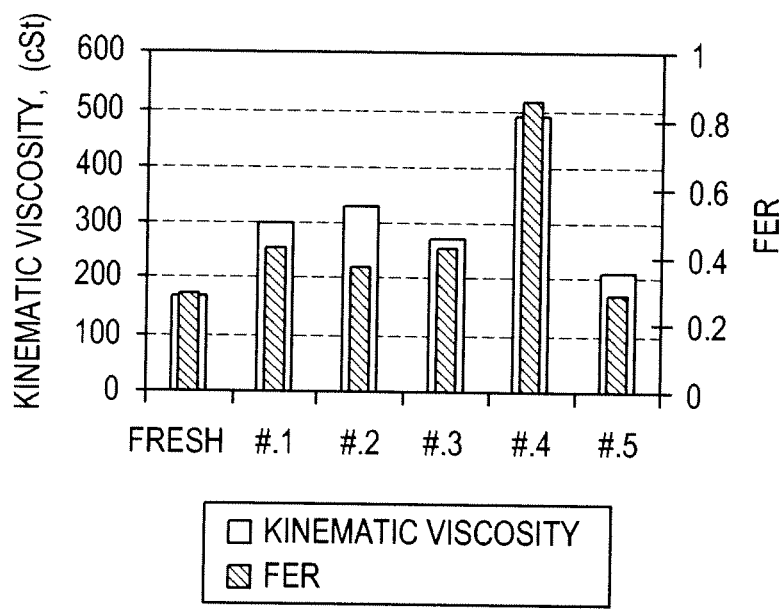
FIG. 13 is a graph showing kinematic viscosities and oil oxidation, which are measured from different types of oil samples at room temperature through the method of the present invention.
Figure 14:
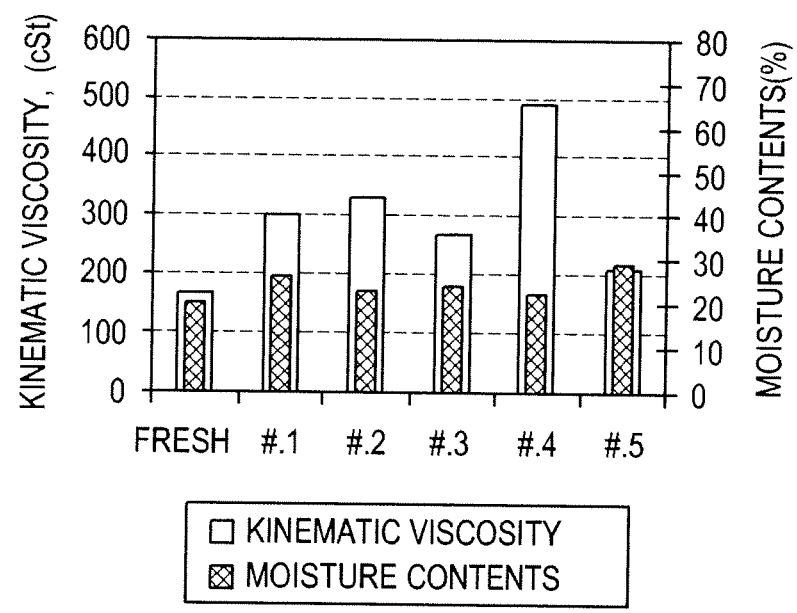
FIG. 14 is a graph showing kinematic viscosities and moisture contents, which are measured from different types of oil samples at room temperature through the method of the present invention.

FIG. 13 is a graph showing kinematic viscosities and oil oxidation which are measured from different kinds of oil samples (e.g., including fresh oil and a used oil) at air temperature through the method according to one embodiment. FIG. 14 is a graph showing kinematic viscosities and moisture contents which are measured from different kinds of oil samples (e.g., including a fresh oil and a used oil) at room temperature through the method according to one embodiment. In the measurement, the fresh oil was "T46" available from Mobil Co. Further, the used oil was obtained after a fresh oil used in five different compressors under an ambient temperature condition. As shown in FIG. 13, the FER of the fresh oil and the used oil changes similarly to the kinematic viscosity. As shown in FIG. 14, the moisture contents in the five used oil are nearly equal to the moisture contents in the fresh oil. Accordingly, it can be ascertained that the FER functions as one factor affecting the change of the oil viscosity.

In the foregoing embodiments, the magnetoelastic ribbon is fixed to the housing. Thus, the oil viscosity can be measured more accurately. Further, since the threads are formed on the housing of the probe, the probe can be easily coupled to and separated from the oil containing member. Furthermore, because the probe has the protective mesh at the one end of the housing, the protective mesh can prevent mechanical damages on the magnetoelastic ribbon and prevent air bubbles from approaching the magnetoelastic ribbon.

According to the foregoing embodiments, it is possible to measure the oil viscosity in real time and to display the measured values through the LCD or the status indicator. Accordingly, the oil can be replaced in a timely manner in terms of the change of the oil viscosity, thereby prolonging the service life of machines or equipments. Further, since the natural frequency of the magnetoelastic ribbon in the air is compensated in accordance with the oil temperature, the oil viscosity can be measured in real time more accurately. Furthermore, since the oil viscosity monitoring apparatus includes the moisture sensor and the oxidation sensor, it is possible to monitor the moisture contents in the oil and the oxidation of the oil together with the oil viscosity.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A probe for measuring an oil viscosity, comprising:
a housing mounted to a member for containing an oil and made from a non-magnetic material;
a magnetoelastic ribbon fixed to an inside of the housing through a first insert member at one end and at least partially immersed in the oil at an opposite end;
an electromagnetic coil embedded to the housing so as not to contact the oil and to surround the magnetoelastic ribbon;
a temperature sensor coupled or fitted to one end of the housing for measuring a temperature of the oil; and
an electrical board electrically connected to the electromagnetic coil and the temperature sensor, and fixed to an opposite end of the housing through a second insert member and a cover, a protective mesh attached to the one end of the housing and preventing air bubbles in the oil from approaching the magnetoelastic ribbon.

2. The probe of claim 1, further comprising a moisture sensor coupled or fitted to the one end of the housing and electrically connected to the electrical board for measuring moisture contained in the oil.

3. An apparatus for monitoring an oil viscosity, comprising:
a housing mounted to a member for containing an oil;
a viscosity sensor including a magnetoelastic ribbon and an electromagnetic coil;
a temperature sensor mounted to the housing for measuring a temperature of the oil;
an electrical board electrically connected to the viscosity sensor and the temperature sensor; and
an electronic module electrically connected to the electrical board,
wherein one end of the magnetoelastic ribbon is fixed to an inside of the housing through a first insert member and an opposite end of the magnetoelastic is at least partially immersed in the oil;
the electromagnetic coil is disposed in the housing to surround the magnetoelastic ribbon;
the electronic module comprises a microprocessor, a comparator, and a memory;
the electromagnetic coil is supplied with a DC bias voltage and an AC excitation voltage;
the comparator receives a signal $S_{oil}$ induced in the electromagnetic coil while shutting off the AC excitation voltage, compares the signal $S_{oil}$ with a reference voltage, outputs and sends results to the microprocessor;
the microprocessor estimates a natural frequency $f_{n\text{-}oil}(T)$ of the magnetoelastic ribbon in the oil at the temperature T based on the results from the comparator;
the microprocessor estimates a natural frequency $f_{n\text{-}air}(T)$ of the magnetoelastic ribbon in the air at the temperature T or receives the natural frequency $f_{n\text{-}air}(T)$ of the magnetoelastic ribbon in the air at the temperature T from the memory;
the microprocessor calculates a difference in natural frequency $\Delta f$ of the magnetoelastic ribbon in the oil and the air at the temperature; and
the microprocessor calculates an acoustic viscosity AV, a kinematic viscosity $v$ and a dynamic viscosity $\eta$ by the following equations:

$$AV = \eta \rho_L = \Delta f^2 \frac{8\pi \rho_s d^2}{f_{n\_air}(T)};$$

$$v = \frac{AV}{\rho_L^2}; \text{ and}$$

-continued $$\eta = \frac{AV}{\rho_L};$$

wherein $\rho_s$ is a density of the magnetoelastic ribbon and d is a thickness of the magnetoelastic ribbon.

4. The apparatus of claim 3, wherein the electronic module includes:
 a control part for controlling an operation of the viscosity sensor and the temperature sensor connected to the electrical board and processing a signal received from the viscosity sensor and the temperature sensor;
 a display part for displaying values processed by the control part; and
 an operation part for operating the control part,
 wherein the control part comprises the microprocessor, the comparator, and the memory;
 the comparator judges whether the acoustic viscosity AV, the kinematic viscosity $\nu$ and the dynamic viscosity $\eta$ are lower than first threshold values, or higher than second threshold values or between the first threshold and the second threshold values; and
 the display part display the compared values.

5. The apparatus of claim 3, wherein the electronic module further comprises an analog-to-digital converter, a programmable counter array, a mixer, and a DC voltage source;
 the analog-to-digital converter converts an analog signal from the temperature sensor to a digital signal, and send the digital signal to the microprocessor;
 the microprocessor sends an AC excitation voltage to the mixer through the programmable counter array; and
 the mixer mixes the AC excitation voltages and a DC bias voltage received from the DC voltage source, and sends the mixed voltages to the viscosity sensor.

6. The apparatus of claim 5, further comprising a moisture sensor mounted to the housing and electrically connected to the electrical board for measuring moisture contained in the oil,
 wherein the electronic module further comprises a matcher; and
 an analog signal from the moisture sensor is matched through the matcher and is converted to a digital signal through the analog-to-digital converter, and then is sent to the microprocessor.

7. The apparatus of claim 3, further comprising an oxidation sensor mounted to the housing for measuring an oil oxidation.

8. The apparatus of claim 6, wherein the electronic module further comprises a low-pass filter and an amplifier; and a signal from the viscosity sensor is sent to the microprocessor through the low-pass filter and the amplifier.

* * * * *